(12) United States Patent
Shribak et al.

(10) Patent No.: US 7,202,950 B2
(45) Date of Patent: Apr. 10, 2007

(54) RETARDANCE MEASUREMENT SYSTEM AND METHOD

(75) Inventors: Mykhailo Shribak, Woods Hole, MA (US); Rudolf Oldenbourg, Falmouth, MA (US)

(73) Assignee: Marine Biological Laboratory, Woods Hole, MA (US)

( * ) Notice: Subject to any disclaimer, the term of this patent is extended or adjusted under 35 U.S.C. 154(b) by 400 days.

(21) Appl. No.: 10/616,080

(22) Filed: Jul. 8, 2003

(65) Prior Publication Data

US 2005/0007590 A1    Jan. 13, 2005

(51) Int. Cl.
*G01J 4/00* (2006.01)

(52) U.S. Cl. .................................... 356/364

(58) Field of Classification Search ............... None
See application file for complete search history.

(56) References Cited

U.S. PATENT DOCUMENTS

| | | | |
|---|---|---|---|
| 5,521,705 A | | 5/1996 | Oldenbourg et al. |
| 5,788,632 A | * | 8/1998 | Pezzaniti et al. ............ 600/316 |
| 6,501,548 B1 | | 12/2002 | Oldenbourg |
| 6,697,157 B2 | * | 2/2004 | Wang et al. ................. 356/364 |

FOREIGN PATENT DOCUMENTS

GB   2 310 925   9/1997

OTHER PUBLICATIONS

E. A. Patterson, W. Ji, and Z. Fwang, "On Image Analysis For Birefringence Measurements in Photoelasticity", Optic Laser Engineering, 28, pp. 17-36, 1997.

S. Inoué, "A Method For Measuring Small Retardations of Structures in Living Cells", Exp. Cell Res. 2, pp. 513-517, 1951.

S.Inoué and R. Oldenbourg, Microscopes, in *Handbook of Optics*, M. Bass, Editor. 1995, McGraw-Hill, Inc. New York. pp. 17.1-17.52.

M. Noguchi, T. Ishikawa, M. Ohno, and S. Tachihara, "Measurement of 2D Birefringence Distribution," in *International Symposium on Optical Fabrication, Testing, and Surface Evaluation*, Jumpei Tsujiuchi, ed., Proc. SPIE 1720, 367-378, 1992.

Y. Otani, T. Shimada, T. Yoshizawa, "The Local-Sampling Phase Shifting Technique For Precise Two-Dimensional Birefringence Measurement", *Optical Review*, 1(1), pp. 103-106, 1994.

J. L. Pezzanitti, and R. A. Chipman, "Mueller Matrix Imaging Polarimetry", *Opt. Eng.* 34(6), pp. 1558-1568, 1995.

Y. Zhu, T. Koyama, T. Takada, and Y. Murooka, "Two-Dimensional Measurement Technique For Birefringence Vector Distributions: Measurement Principle," *Appl. Opt.* 38, pp. 2225-2231, 1999.

(Continued)

*Primary Examiner*—Tu T. Nguyen
(74) *Attorney, Agent, or Firm*—Cohen Pontani Liberman & Pavane LLP

(57) ABSTRACT

In an apparatus and method for measuring retardance and slow axis azimuth in sample specimens, a sample is illuminated by circularly polarized monochromatic light which is then analyzed by an elliptical analyzer at different settings. In another embodiment, light conditioned by an elliptical polarizer at various settings illuminates a specimen and the beam exiting the sample is analyzed by a circular analyzer. The elliptical analyzer/polarizer may have selectable ellipticity and azimuth angle, including in some cases a setting of circular polarization. Background images obtained with selected settings of the elliptical analyzer/polarizer, but without the sample present, are used in some embodiments to improve the measurement.

20 Claims, 10 Drawing Sheets

OTHER PUBLICATIONS

A. M. Glazer, J. G. Lewis, and W. Kaminsky, "An Automatic Optical Imaging System For Birefringent Media," *Proc. R. Soc. Lond.* A 452, pp. 2751-2765, 1996.

M. I. Shribak "Autocollimating Detectors of Birefringence", in International Conference on Optical Inspection and Micromeasurements, Christophe Gorecki, Editors, Proc.SPIE 2782, pp. 805-813, 1996.

M. I. Shribak, Y. Otani and T. Yoshizawa, "Return-Path Polarimeter For Two Dimensional Birefringence Distribution Measurement", Polarization: Measurement, Analysis, and Remote Sensing II, Dennis H., Goldstein; and David B. Chenault; Eds. Proc., SPIE 3754, pp. 144-149, 1999.

\* cited by examiner

| Setting | Beam parameters | | Retardances (Fig 1A) | | Retardances (Fig 1B) | |
| --- | --- | --- | --- | --- | --- | --- |
| | $\varepsilon$ | $\gamma$ | $\alpha$ | $\beta$ | $\alpha$ | $\beta$ |
| $\Sigma_0$ | 45° | NA | 90° | 180° | 270° | 0° |
| $\Sigma_1$ | 45°-$\chi$/2 | 0° | 90°-$\chi$ | 180° | 270°-$\chi$ | 0° |
| $\Sigma_2$ | 45°-$\chi$/2 | 90° | 90°+$\chi$ | 180° | 270°+$\chi$ | 0° |
| $\Sigma_3$ | 45°-$\chi$/2 | 45° | 90° | 180°-$\chi$ | 90°-$\chi$ | 180° |
| $\Sigma_4$ | 45°-$\chi$/2 | 135° | 90° | 180°+$\chi$ | 90°+$\chi$ | 180° |

Fig. 4

N=2 ALGORITHM

TAKE BACKGROUND IMAGES, SPECIMEN OUT

*CREATE CIRCULAR SETTING OF POLARIZER $\Sigma_0$ / CIRCULAR ANALYZER*
↓
*CAPTURE AND STORE IMAGE $I_{BG0}$*
↓
*CREATE ELLIPTICAL SETTING OF POLARIZER $\Sigma_1$ / CIRCULAR ANALYZER*
↓
*CAPTURE AND STORE IMAGE $I_{BG1}$*
↓
*CREATE ELLIPTICAL SETTING OF POLARIZER $\Sigma_3$ / CIRCULAR ANALYZER*
↓
*CAPTURE AND STORE IMAGE $I_{BG3}$*
↓

TAKE IMAGES WITH SPECIMEN IN

*CREATE ELLIPTICAL SETTING OF POLARIZER $\Sigma_1$ / CIRCULAR ANALYZER*
↓
*CAPTURE AND STORE IMAGE $I_1$*
↓
*CREATE ELLIPTICAL SETTING OF POLARIZER $\Sigma_3$ / CIRCULAR ANALYZER*
↓
*CAPTURE AND STORE IMAGE $I_3$*
↓
*COMPUTE TERMS A AND B FROM $I_1$, $I_3$, $I_{BG0}$, $I_{BG1}$, $I_{BG3}$'*
↓
*COMPUTE RETARDANCE $\Delta$ AND AZIMUTH $\varphi$ FROM A AND B AND STORE*

Fig. 5

N=3 ALGORITHM

TAKE BACKGROUND IMAGES, SPECIMEN OUT

*CREATE ELLIPTICAL SETTING OF POLARIZER $\Sigma_1$ / CIRCULAR ANALYZER*
↓
*CAPTURE AND STORE IMAGE $I_{BG1}$*
↓
*CREATE ELLIPTICAL SETTING OF POLARIZER $\Sigma_2$ / CIRCULAR ANALYZER*
↓
*CAPTURE AND STORE IMAGE $I_{BG2}$*
↓
*CREATE ELLIPTICAL SETTING OF POLARIZER $\Sigma_3$ / CIRCULAR ANALYZER*
↓
*CAPTURE AND STORE IMAGE $I_{BG3}$*
↓
COMPUTE TERMS $A_{BG}$ AND $B_{BG}$ FROM $I_{BG1}$, $I_{BG2}$, $I_{BG3}$, AND STORE

Fig. 6

N=3 ALGORITHM

TAKE IMAGES WITH SPECIMEN IN

CREATE ELLIPTICAL SETTING OF POLARIZER $\Sigma_1$ / CIRCULAR ANALYZER
↓
CAPTURE AND STORE IMAGE $I_1$
↓
CREATE ELLIPTICAL SETTING OF POLARIZER $\Sigma_2$ / CIRCULAR ANALYZER
↓
CAPTURE AND STORE IMAGE $I_2$
↓
CREATE ELLIPTICAL SETTING OF POLARIZER $\Sigma_3$ / CIRCULAR ANALYZER
↓
CAPTURE AND STORE IMAGE $I_3$
↓
COMPUTE TERMS *A* AND *B* FROM $I_1, I_2, I_3$
↓
COMPUTE CORRECTED TERMS $A' = A - A_{BG}$ AND $B' = B - B_{BG}$
↓
COMPUTE RETARDANCE $\Delta$ AND AZIMUTH $\varphi$ FROM *A'* AND *B'* AND STORE

Fig. 7

N=4 ALGORITHM

TAKE BACKGROUND IMAGES, SPECIMEN OUT

CREATE ELLIPTICAL SETTING OF POLARIZER $\Sigma_1$ / CIRCULAR ANALYZER
↓
CAPTURE AND STORE IMAGE $I_{BG1}$
↓
CREATE ELLIPTICAL SETTING OF POLARIZER $\Sigma_2$ / CIRCULAR ANALYZER
↓
CAPTURE AND STORE IMAGE $I_{BG2}$
↓
CREATE ELLIPTICAL SETTING OF POLARIZER $\Sigma_3$ / CIRCULAR ANALYZER
↓
CAPTURE AND STORE IMAGE $I_{BG3}$
↓
CREATE ELLIPTICAL SETTING OF POLARIZER $\Sigma_4$ / CIRCULAR ANALYZER
↓
CAPTURE AND STORE IMAGE $I_{BG4}$
↓
COMPUTE TERMS $A_{BG}$ AND $B_{BG}$ FROM $I_{BG1}, I_{BG2}, I_{BG3}, I_{BG4}$ AND STORE

Fig. 8

N=4 ALGORITHM

TAKE IMAGES WITH SPECIMEN IN

*CREATE ELLIPTICAL SETTING OF POLARIZER $\Sigma_1$ / CIRCULAR ANALYZER*
↓
*CAPTURE AND STORE IMAGE $I_1$*
↓
*CREATE ELLIPTICAL SETTING OF POLARIZER $\Sigma_2$ / CIRCULAR ANALYZER*
↓
*CAPTURE AND STORE IMAGE $I_2$*
↓
*CREATE ELLIPTICAL SETTING OF POLARIZER $\Sigma_3$ / CIRCULAR ANALYZER*
↓
*CAPTURE AND STORE IMAGE $I_3$*
↓
*CREATE ELLIPTICAL SETTING OF POLARIZER $\Sigma_4$ / CIRCULAR ANALYZER*
↓
*CAPTURE AND STORE IMAGE $I_4$*
↓
*COMPUTE TERMS A AND B FROM $I_1, I_2, I_3, I_4$*
↓
*COMPUTE CORRECTED TERMS $A'=A-A_{BG}$ AND $B'=B-B_{BG}$*
↓
*COMPUTE RETARDANCE $\Delta$ AND AZIMUTH $\varphi$ FROM $A'$ AND $B'$ AND STORE*

Fig. 9

N=5 ALGORITHM

TAKE BACKGROUND IMAGES, SPECIMEN OUT

*CREATE CIRCULAR SETTING OF POLARIZER $\Sigma_0$ / CIRCULAR ANALYZER*
↓
*CAPTURE AND STORE IMAGE $I_{BG0}$*
↓
*CREATE ELLIPTICAL SETTING OF POLARIZER $\Sigma_1$ / CIRCULAR ANALYZER*
↓
*CAPTURE AND STORE IMAGE $I_{BG1}$*
↓
*CREATE ELLIPTICAL SETTING OF POLARIZER $\Sigma_2$ / CIRCULAR ANALYZER*
↓
*CAPTURE AND STORE IMAGE $I_{BG2}$*
↓
*CREATE ELLIPTICAL SETTING OF POLARIZER $\Sigma_3$ / CIRCULAR ANALYZER*
↓
*CAPTURE AND STORE IMAGE $I_{BG3}$*
↓
*CREATE ELLIPTICAL SETTING OF POLARIZER $\Sigma_4$ / CIRCULAR ANALYZER*
↓
*CAPTURE AND STORE IMAGE $I_{BG4}$*
↓
*COMPUTE TERMS $A_{BG}$ AND $B_{BG}$ FROM $I_{BG0}, I_{BG1}, I_{BG2}, I_{BG3}, I_{BG4}$ AND STORE*

Fig. 10

N=5 ALGORITHM

TAKE IMAGES WITH SPECIMEN IN

*CREATE CIRCULAR SETTING OF POLARIZER $\Sigma_0$ / CIRCULAR ANALYZER*
↓
*CAPTURE AND STORE IMAGE $I_0$*
↓
*CREATE ELLIPTICAL SETTING OF POLARIZER $\Sigma_1$ / CIRCULAR ANALYZER*
↓
*CAPTURE AND STORE IMAGE $I_1$*
↓
*CREATE ELLIPTICAL SETTING OF POLARIZER $\Sigma_2$ / CIRCULAR ANALYZER*
↓
*CAPTURE AND STORE IMAGE $I_2$*
↓
*CREATE ELLIPTICAL SETTING OF POLARIZER $\Sigma_3$ / CIRCULAR ANALYZER*
↓
*CAPTURE AND STORE IMAGE $I_3$*
↓
*CREATE ELLIPTICAL SETTING OF POLARIZER $\Sigma_4$ / CIRCULAR ANALYZER*
↓
*CAPTURE AND STORE IMAGE $I_4$*
↓
*COMPUTE TERMS A AND B FROM $I_0$, $I_1$, $I_2$, $I_3$, $I_4$*
↓
*COMPUTE CORRECTED TERMS $A'=A-A_{BG}$ AND $B'=B-B_{BG}$*
↓
*COMPUTE RETARDANCE $\Delta$ AND AZIMUTH $\varphi$ FROM $A'$ AND $B'$ AND STORE*

Fig. 11

RETARDANCE MEASUREMENT SYSTEM AND METHOD

BACKGROUND OF THE INVENTION

1. Field of the Invention

The present invention is related to polarized light and, more particularly, to measurement of retardance and slow axis azimuth angle, and most especially to systems that produce images of these properties in a two-dimensional image of a sample.

2. Description of the Related Art

Measuring of two-dimensional birefringence distributions is an established technique for analyzing the structure of various specimens. It can also be applied to study the vector or tensor fields associated with birefringence.

The application of two-dimensional birefringence measurements to the analysis of inner stress in construction models using photoelasticity is also well known (*Handbook on Experimental Mechanics*, Ed. by Albert S. Kobayashi, Prentice Hall: Englewood Cliffs, 1987). E. A. Patterson and co-authors offered a full-field imaging polariscope (E. A. Patterson, W. Ji, and Z. Fwang, "On Image Analysis For Birefringence Measurements in Photoelasticity", Optic Laser Engineering, 28, pp. 17–36, 1997). It has a circularly polarized illumination beam and six consecutive settings of an analyzer polarizer: left and right circular polarized settings and four linear polarized settings at 0°, 45°, 90° and 135°.

The technique doesn't provide high sensitivity with low retardance specimens, and describes use of a polarization state analyzer comprising a rotated quarter waveplate and rotated linear analyzer.

Imaging polarization techniques have been important for microscope studies of biological specimens (S. Inoué, "A Method For Measuring Small Retardations of Structures in Living Cells", Exp. Cell Res. 2, pp.513–517, 1951; S. Inoue and K. R. Spring, *Video Microscopy. The Fundamentals*, $2_{nd}$ ed., New York: Plenum Press, 1997; S. Inoué and R. Oldenbourg, *Microscopes*, in *Handbook of Optics*, M. Bass, Editor. 1995, McGraw-Hill, Inc.: New York. pp. 17.1–17.52).

Other systems for imaging measurement systems with rotated optical polarization elements have been shown (M. Noguchi, T. Ishikawa, M. Ohno, and S. Tachihara, "Measurement of 2D Birefringence Distribution," in *International Symposium on Optical Fabrication, Testing, and Surface Evaluation*, Jumpei Tsujiuchi, ed., Proc. SPIE 1720, 367–378,1992; Y. Otani, T. Shimada, T. Yoshizawa, "The Local-Sampling Phase Shifting Technique For Precise Two-Dimensional Birefringence Measurement", *Optical Review*, 1(1), pp.103–106, 1994).

J. L. Pezzanitti, and R. A. Chipman proposed a device for measuring Muller matrix coefficients, comprising a polarization state generator and polarization state analyzer. (J. L. Pezzanitti, and R. A. Chipman, "Mueller Matrix Imaging Polarimetry", *Opt. Eng.* 34(6), pp.1558–1568, 1995). The generator and analyzer are created by fixed linear polarizers with parallel transmittance axes and two waveplates, which are rotated with a 5:1 ratio. The waveplate retardances are the same, equal to one-quarter or one-third wavelength. At least 25 consecutive images are required in order to determine a Muller matrix, and in the example given the authors acquire a total of 60 images per measurement.

Y. Zhu and coauthors described two-dimensional techniques for birefringence measurement (Y. Zhu, T. Koyama, T. Takada, and Y. Murooka, "Two-Dimensional Measurement Technique For Birefringence Vector Distributions: Measurement Principle," *Appl. Opt.* 38, pp. 2225–2231, 1999). A specimen is illuminated by a beam at three polarization states: one linearly polarized and two elliptically polarized with the same ellipticity value and opposite ellipticity sign, which are obtained by mechanically rotated optical elements. A total of six images are used to obtain the two-dimensional retardance and slow axis azimuth distribution.

A birefringence-mapping device, which contains a mechanically rotated linear polarizer and circular analyzer was described by Glazier and Cosier in 1997 (A. M. Glazer, and J. Cosier, "Method and Apparatus For Indicating Optical Anisotropy," UK Patent Application No. 2,310,925). Typically, six images of a specimen are taken while the linear polarizer is incremented in 30° steps; these images. are then processed to yield the birefringence map, as described in an article (A. M. Glazer, J. G. Lewis, and W. Kaminsky, "An Automatic Optical Imaging System For Birefringent Media," *Proc. R. Soc. Lond.* A 452, pp. 2751–2765, 1996). The device is not suitable for measuring low retardance specimens because it is strongly susceptible to light intensity variations, photon statistical noise, detector read-out noise, and digitization error.

Devices with return-path techniques have also been described, by M. I. Shribak "Autocollimating Detectors of Birefringence", in International Conference on Optical Inspection and Micromeasurements, Christophe Gorecki, Editors, Proc.SPIE 2782, pp.805–813, 1996; and by M. I. Shribak, Y. Otani and T. Yoshizawa, "Return-Path Polarimeter For Two Dimensional Birefringence Distribution Measurement", Polarization: Measurement, Analysis, and Remote Sensing II, Dennis H., Goldstein; and David B. Chenault; Eds. Proc., SPIE 3754, pp. 144–149, 1999.

R. Oldenbourg and G. Mei described a method for measurement of retardance and slow-axis azimuth distribution using two techniques: three elliptical and one circular polarized state of illumination beam and circular analyzer; circular polarized state of illumination beam and three consecutive elliptical and one circular polarized setting of analyzer in "Polarized Light Microscopy," U.S. Pat. No. 5,521,705.

R. Oldenbourg describes a background correction procedure in "Retardance Measurement Method," U.S. Pat. No. 6,501,548. The method is based on using a universal compensator as an elliptical polarizer/analyzer which is formed by a pair of variable liquid crystal retarders and a linear polarizer.

While there have thus been shown various techniques for retardance measurement and two-dimensional retardance imaging, the existing techniques in the art require taking six or more readings; or are not well-suited to measurement of low-retardance samples; or do not operate with high speed; or offer less than adequate accuracy or noise.

SUMMARY OF THE INVENTION

The present invention provides apparatus and methods for measuring retardance and principal plane azimuth distribution in samples. It provides for unsurpassed accuracy and low noise in one embodiment, which requires 4 or 5 intensity readings per measurement. In another embodiment, it provides a measurement of retardance and principal plane azimuth distribution from as few as two or three specimen readings together with background readings that are taken once and need not be repeated with each measurement. Thus the present invention provides full information about retardance and azimuth angle with improved noise than the prior art, or with fewer readings required per measurement, or both. It is well-suited for use with an imaging detector to produce two-dimensional retardance images of a specimen. These and other aspects of the invention will be clear from the description provided below.

In accordance with the invention, a specimen is illuminated by circularly polarized monochromatic light and the beam exiting the specimen is analyzed with an elliptical analyzer at different settings, and its intensity is noted. In another embodiment light conditioned by an elliptical polarizer at different settings illuminates a specimen and then passes through a circular analyzer and its intensity is measured. The elliptical analyzer/polarizer can change the degree of ellipticity and azimuth angle, including a setting with circular polarization. In addition, the invention includes the step of taking images at the same settings of the elliptical analyzer/polarizer without the specimen present, for purposes of background correction.

The invention uses the following novel algorithms to produce retardance measurements:

two specimen images with elliptical settings and three or two background images;

three specimen images with elliptical settings;

four specimen images with elliptical settings without extinction setting;

five specimen images with four elliptical settings and one extinction setting.

These algorithms allow one to optimize the measurement for speed, sensitivity, and accuracy. The highest accuracy can be achieved using the 5-frame technique, and in the 4-frame algorithm without extinction setting. Alternatively, when high acquisition speed is important, as when imaging a moving sample, the two-frame algorithm or three-frame algorithm is valuable.

These various algorithms can be employed for polarization imaging systems using different optical configurations to produce the required, elliptical and/or circular illumination and analyzer functions. Suitable apparatus for practicing the invention includes variable retarders such as liquid crystal and electro optical waveplates; waveplates with variable azimuth; fixed waveplates such as quartz or polymer retarders that are mechanically engaged or re-oriented as needed; Faraday rotators; and, indeed, any optical element that performs the required function can be employed. The choice of one optical element over another will be made according to the requirements of the application at hand for measurement speed, size, accuracy, cost, complexity, and other design criteria that may be relevant.

Although the invention is described with specific reference to its use in microscope systems, it can be practiced using a variety of optical systems and is not inherently limited or restricted to use with small samples or in microscopy settings. It can be operated with samples that are viewed in transmission or in reflection. Similarly, although special attention is paid to producing a two-dimensional retardance map, for which the invention is well-suited, the invention can be practiced when a lesser number of retardance measures are needed, or even a single point needs to be measured. Indeed, it is specifically intended that the present invention may be practiced in any context in which it is useful to measure retardance in a sample. Accordingly, it is intended that wherever this description speaks of taking a specimen image (to denote a measurement of intensity across a two-dimensional image), one should understand that it is also possible to implement a comparable system that takes a single point measurement of intensity, or a measurement of intensity at a plurality of points in a line, or a measurement of intensity in any spatial format that is of interest for a given application; and similarly, whenever this description speaks of taking an intensity reading, one should understand that to mean a single point reading of intensity, a two-dimensional image of intensity, or a measurement of intensity in any spatial format that is of interest.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

In the drawings, wherein like reference characters denote similar elements throughout the various Figures:

FIG. 4 is a table illustrating examples of polarization settings of the probe beam with ellipticity $\epsilon$ and major axis azimuth $\gamma$ and the corresponding retardances $\alpha$ and $\beta$ of liquid crystal plates 114 and 115 whose optical axes 116 and 117 are oriented at angles of 45° and 22.5° to each other, respectively;

FIG. 5 is a simplified flow-chart illustrating a sequence of elliptical polarizer settings used with the apparatus of FIG. 1 for birefringence mapping using the two-image algorithm;

FIG. 6 is a simplified flow-chart illustrating a sequence of elliptical polarizer settings used with the apparatus of FIG. 1 for background birefringence mapping using the three-image algorithm;

FIG. 7 is a simplified flow-chart illustrating a sequence of elliptical polarizer settings used with the apparatus of FIG. 1 for specimen birefringence mapping using the three-image algorithm;

FIG. 8 is a simplified flow-chart illustrating a sequence of elliptical polarizer settings used with the apparatus of FIG. 1 for background birefringence mapping using the four-image algorithm;

FIG. 9 is a simplified flow-chart illustrating a sequence of elliptical polarizer settings used with the apparatus of FIG. 1 for specimen birefringence mapping using the four-image algorithm;

FIG. 10 is a simplified flow-chart illustrating a sequence of elliptical polarizer settings used with the apparatus of FIG. 1 for background birefringence mapping using the five-image algorithm; and FIG. 11 is a simplified flow-chart illustrating a sequence of elliptical polarizer settings used with the apparatus of FIG. 1 for specimen birefringence mapping using the five-image algorithm.

DETAILED DESCRIPTION OF THE PRESENTLY PREFERRED EMBODIMENTS

Figure 1:
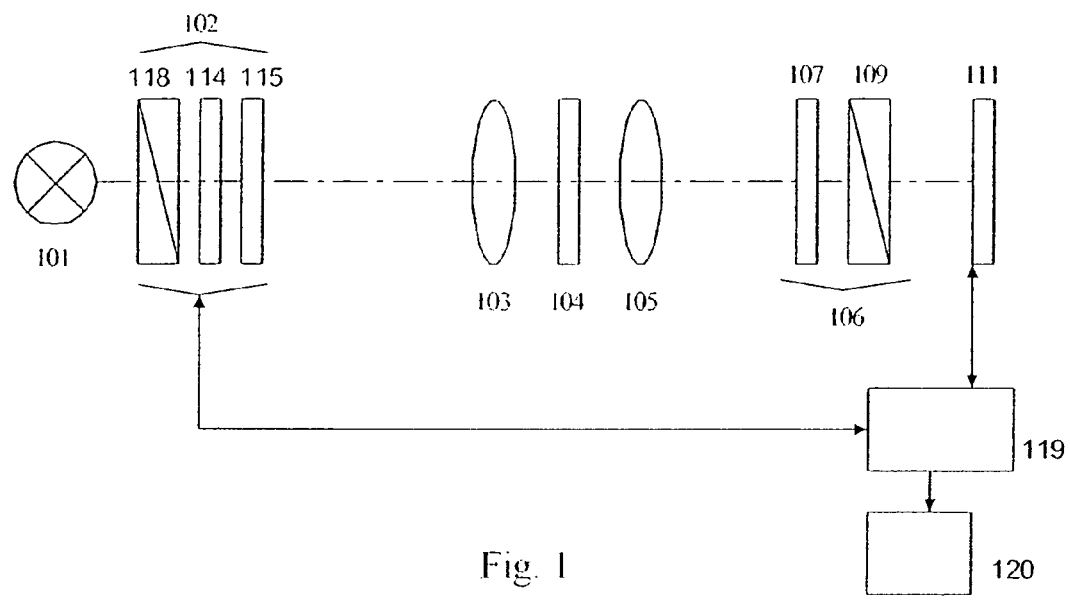
FIG. 1 is a schematic drawing implementing the invention in a first optical arrangement to construct the variable elliptical polarizers.

Optical configurations suitable for practicing the invention in a microscope are shown in schematic form in FIG. 1. The apparatus consists of the following elements in series: monochromatic light source 101, a variable elliptical polarizer 102, a condenser 103, the specimen 104, an objective lens 105, a right or left circular analyzer 106 comprising quarter waveplate 107 with retardance of λ/4 and fast axis at azimuth angle of ±45° and linear analyzer 109 with a transmission axis at azimuth angle of 0°, and imaging detector 111. The detector and polarizer are in communication with processor 119, which receives the photodetector signals and performs the calculations of retardance; and optional display 120, which provides images of the retardance to an operator or user.

The monochromatic light source may operate in the visible, the ultraviolet, or the infrared, according to what is desired. The detector and other elements should be responsive in the selected wavelength band, as is known to those skilled in the art. In this context, monochromatic means a narrow range of wavelengths, but need not be literally a single wavelength such as a laser emits. A broadband lamp and filter may be used successfully.

Figure 2:
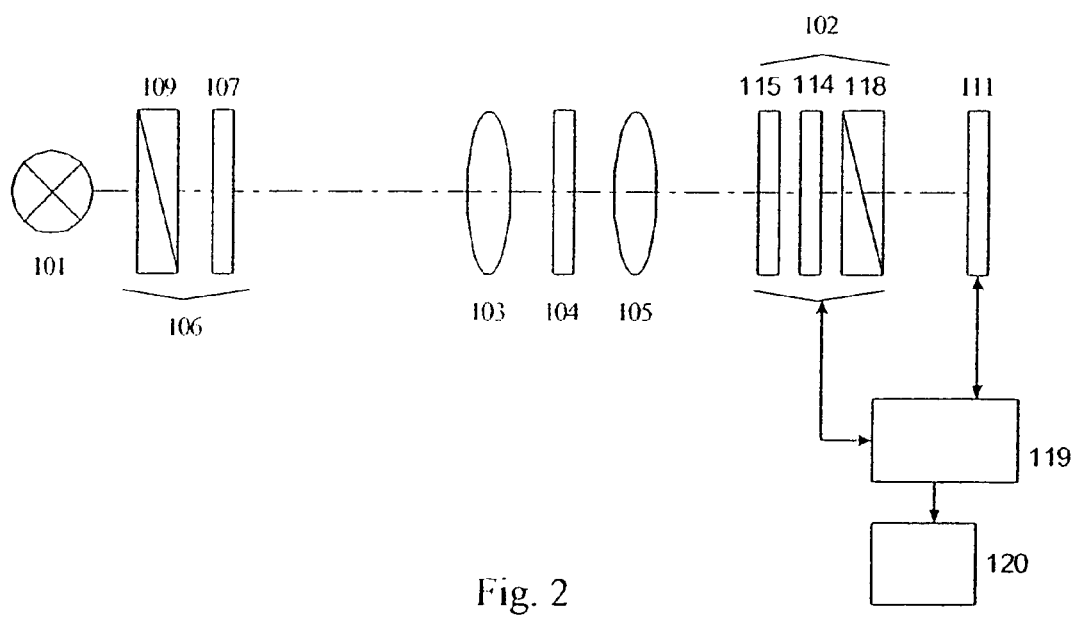
FIG. 2 is a schematic drawing implementing the invention in a second optical arrangement to construct the variable elliptical polarizers.

Another set of optical configurations suitable for practicing the invention is shown in schematic form in FIG. 2. These consist of an illuminator 101, a right or left circular polarizer 106 comprising linear polarizer 109 with transmission axis at azimuth angle of 0° and quarter waveplate 107 with retardance λ/4 and fast axis azimuth at ±45° sample 106, objective lens 105, and a variable elliptical analyzer 102 in the imaging path.

The variable elliptical polarizer 102 is further made up from liquid crystal retarder cells 114 and 115, adjacent a linear polarizer 118. In the apparatus of FIG. 1, the angle between the polarizer transmission axis and the crystal axis of retarder 114 is +/−45°, and between the crystal axis of retarder 114 and the crystal axis of retarder 115 is +/−45°. In the apparatus of FIG. 2, the angle between the polarizer transmission axis and the crystal axis of retarder 114 is +/−22.5° or +/−67.5°, and the angle between the crystal axis of retarder 114 and the crystal axis of retarder 115 is +/−22.5° or +/−67.5°.

While here and throughout this disclosure these angles and retardances are specified precisely and with their ideal value, it is possible to construct a system in accordance with the invention using real components, for which the actual angles and retardances will vary from these values. One may determine what deviation from these idealized values is acceptable either by mathematical simulation or by direct measurement and test.

First, consider the configuration of FIG. 1 with a left circular analyzer and the elliptical polarizer. The elliptical polarizer can express one circular and four elliptical polarization states that can be used for capturing the raw images. The positions of the corresponding polarization states on the Poincare sphere are given in FIG. 3 as $\chi_0$ through $\chi_{102\,4}$, and $E_1$, $E_2$, $E_3$ and $E_4$ are the vibration ellipses of these states.

The Poincare sphere is an established way of representing state of polarization, where each point on the sphere indicates a unique polarization state of light. The longitude $2\theta$ and latitude $2\epsilon$ of a point on the sphere correspond to polarization ellipse with azimuth angle $\theta$ and ellipticity angle $\epsilon$. The ellipticity angle is an auxiliary angle that specifies a shape of the vibration ellipse, via the equation $\tan \epsilon = b/a$, where a and b are the major and minor semi-axes of the ellipse. Thus, lines of constant longitude and latitude on the sphere represent contours of equal azimuth and equal ellipticity, respectively. The Northern hemisphere indicates light with right-hand elliptical polarization, and the Southern hemisphere shows left-hand elliptically polarized light.

Some examples of this are as follows. Right and left circular polarizations correspond to the North Pole and South Pole of the sphere. Each point on the equator represents a distinct linear state of polarization, more specifically, a point with longitude $2\theta$ on the equator corresponds to a linear polarization state with azimuth angle $\theta$; while a point in the north hemisphere having same the longitude but with latitude $2\epsilon$ corresponds to a right-hand elliptically polarized state with the same azimuth angle with an ellipticity angle $\epsilon$.

The extinction setting of the elliptical polarizer when there is no sample retardance corresponds to the North Pole of the sphere. Points that lie on a cone with axis 0Z and the same latitude angle 90°−α describe additional settings $\chi_1$, $\chi_2$, $\chi_3$ and $\chi_4$ with longitude angles of 0°, 180°, 90° and 270° respectively.

Figure 3:
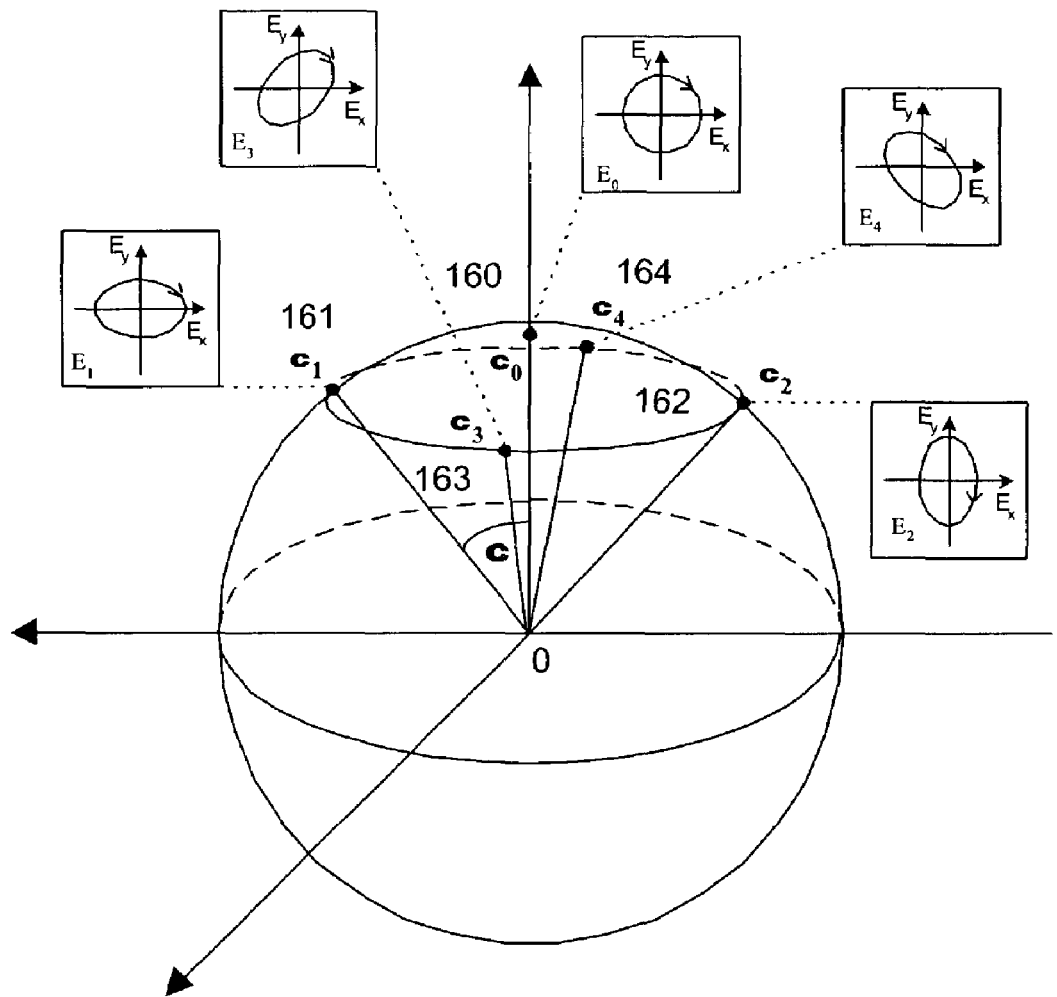
FIG. 3 is a schematic drawing of probe beam settings on the Poincare sphere, in which $\chi_0$ is the setting with right circular polarization, and $\chi_1$, $\chi_2$, $\chi_3$, and $\chi_4$ are settings with elliptical polarizations.

These states $\chi_0$ through $\chi_4$, shown in FIG. 3, are appropriate for practicing the present invention when used in concert with a left circular analyzer. In an analogous manner, one may use an elliptical polarizer to generate a set of elliptical states located similarly about the South Pole of the Poincare sphere together with a right circular analyzer.

Moreover, one can also use polarization states similar to the $\chi_{1-\chi 4}$ just described, except that the longitude on the Poincare sphere is shifted by an angle x in each case. This is equivalent to a coordinate transformation where the azimuth angle is rotated by an angle of x/2. Here and throughout this application, we will treat the case where x=0, but the alternatives with non-zero x work equally well, provided that one corrects the azimuth angles appropriately by x/2 if they are used.

In order to produce the necessary polarization states in the illumination beam we can use a linear polarizer to produce linearly polarized light along an axis of 0°, together with a pair of variable retarder plates with various angles between the slow axes. Examples of two configurations are shown in FIGS. 1 and 2. In the first case of FIG. 1, suitable polarization states can be obtained by the following settings of plates 114 and 115:

$$\chi_0(90°, 180°), \qquad [1a]$$

$$\chi_1(90°-c, 180°), \qquad [1b]$$

$$\chi_2(90°+c, 180°), \qquad [1c]$$

$$\chi_3(90°, 180°-c), \qquad [1d]$$

$$\chi_4(90°, 180°+c) \qquad [1e]$$

where the notation (α°, β°) denotes that the first waveplate 114 has a retardation of a degrees and the second waveplate 115 has a retardation of β degrees. These comprise a circular polarization state, and four states lying at constant latitude of 90°−c on the Poincare sphere, equally spaced in longitude.

In the second configuration of FIG. 2, the angle between slow axes is 22.5°. For this case we obtain the same polarization states with settings:

$$\chi_0(270°, 0°), \qquad [2a]$$

$$\chi_1(270°-c, 0°), \qquad [2b]$$

$$\chi_2(270°+c, 0°), \qquad [2c]$$

$\chi_3(90°-c, 180°)$, [2d]

$\chi_4(90°+c, 180°)$ [2e]

Like the previous case, these also comprise a circular polarization state $\chi_0$ and four equally spaced states $\chi_1$–$\chi_4$ having constant latitude of 90°–c on the Poincare sphere.

These settings are shown in tabular form in FIG. 4 for the apparatus of FIGS. 1 and 2. As will be apparent to those skilled in the art, there are equivalent retarder arrangements that accomplish the same optical function, namely the formation of a polarization analyzer that selects for the chosen states of polarization. Such alternative may be employed if desired, without altering the function of the present invention.

The invention provides for using N states from among the five states $\chi_0$ through $\chi_4$, where N may be 2, 3, 4, or 5, depending on the requirements at hand. The invention is thus a more general set of algorithms that complement the 4-state algorithm described in the Oldenbourg and Mei U.S. Pat. No. 5,521,705. These algorithms are now discussed in turn.

Embodiment with N=2

In one preferred embodiment, N=2 and the states used are $\chi_1$ and $\chi_3$. Images are obtained under these conditions with the sample present, and with no sample. The latter are termed background images, and are used to compensate for residual polarization signature of the apparatus. The quantities A and B are calculated from these as follows:

$A \equiv (I_1-I_{BG1})/I_{BG1} * \tan(c/2)$ [3a]

$B \equiv (I_3-I_{BG3})/I_{BG3} * \tan(c/2)$ [3b]

Here and throughout the remainder of this application, c is per Equations 1a–1e or 2a–2e, $I_i$ indicates that the elliptical polarizer was set to state $\chi_i$ for that measurement, and the subscript BG indicates a background image, taken with no sample present. From A and B the retardance $\delta$ and azimuth angle $\Phi$ are calculated as:

$\delta = \arcsin([A^2+B^2]^{1/2})$ [4a]

$\Phi = \frac{1}{2} \arctan(A/B)$ [4b]

This embodiment exhibits the best speed, since it requires the least time for image acquisition. But its sensitivity is lower than with the other embodiments of the invention where N=3, 4, or 5. It also requires that the sample transmission be essentially unity; as absorption in the sample will distort the retardance readings.

An alternative, shown in FIG. 5 in flowchart form, involves taking an additional background reading with the elliptical polarizer set for the extinction case, i.e. circularly polarized light. The reading thus obtained is termed $I_{BG0}$, and the A and B parameters are calculated using the following equations:

$A \equiv [(I_1-I_{BG1})/(I_{BG1}-I_{BG0})] * \tan(c/2)$ [4c]

$B \equiv [(I_3-I_{BG3})/(I_{BG3}-I_{BG0})] * \tan(c/2)$ [4d]

from which $\delta$ and $\Phi$ are calculated using equations [4a] and [4b].

Embodiment with N=3

In a second embodiment, N=3 and the states used are $\chi_1$, $\chi_2$, and $\chi_3$. From the images, one derives the quantities:

$A = [(I_1-I_3)/(I_1+I_2)] * \tan(c/2)$ [5a]

$B = [(I_2-I_3)/(I_1+I_2)] * \tan(c/2)$ [5b]

from which the retardance $\delta$ and azimuth angle $\Phi$ are calculated as:

$\delta = 2\arctan\{[2^{1/2}Z]/[1+(1-2[Z/\tan(c/2)]^2)^{1/2}]\}$ [6a]

$\Phi = \frac{1}{2}\arctan(A/B) - 22.5°$ [6b]

where $Z = (A^2+B^2)^{1/2}$ [6c]

This embodiment provides better signal-to-noise than the N=2 embodiment, and works well in situations where the optical equipment has a high extinction ratio, such as 200:1 or better.

Embodiment with N=5

In a third embodiment, N=5. All states are used, $\chi_0$–$\chi_4$, to obtain images $I_0$–$I_4$. From these, one determines the quantities A and B as $A \equiv [(I_1-I_2)/(I_1+I_2-2I_0)] * \tan(c/2)$ [7a]

$B \equiv [(I_4-I_3)/(I_4+I_3-2I_0)] * \tan(c/2)$ [7b]

from which the retardance $\delta$ and azimuth $\phi$ are calculated as $\delta = \arctan(Z)$ when $I_1+I_2-2I_0 \geq 0$ [8a]

$\delta = 180° \arctan(Z)$ when $(I_1+I_2-2I_0) < 0$ [8b]

$\Phi = \frac{1}{2}\arctan(A/B)$ [8c]

This embodiment has the highest sensitivity of all the embodiments, and has equal sensitivity for all retardance azimuth values.

Embodiment with N=4

In a fourth embodiment, N=4. The extinction state $\chi_0$ is not used. Instead, the four states used are $\chi_1$, $\chi_2$, $\chi_3$, and $\chi_4$, resulting in images $I_1$–$I_4$. From these, the parameters A and B are calculated as:

$A = [(I_1-I_2)/(I_1+I_2)] \tan(c/2)$ [9a]

$B = [(I_4-I_3)/(I_4+I_3)] \tan(c/2)$ [9b]

from which the retardance $\delta$ and azimuth angle $\Phi$ are calculated as:

$\delta = 2\arctan(Z/[1+(1-[Z/\tan(c/2)]^2)^{1/2}])$ [10a]

$\Phi = \frac{1}{2}\arctan(A/B)$ [10b]

This system offers good sensitivity and, like the previous embodiment, the retardance sensitivity is independent of azimuth angle. However, it requires that the optical apparatus have a high extinction, such as 200:1, for best performance.

For any of the above embodiments that omit one or more of the states $\chi_1$–$\chi_4$, there are equivalent alternatives that can be used equally well. For example, instead of using $\chi_1$ and $\chi_3$, one might use $\chi_3$ and $\chi_2$, or $\chi_2$ and $\chi_4$, and so on. These variations consist of the embodiments described above, except that the elliptical polarizers express states that are shifted on the Poincare sphere by some fixed longitude shift amount x. As noted earlier, this effects a coordinate transformation of x/2 in the resulting azimuth angle, which can be corrected for if desired.

Similarly, one can construct the elliptical polarizers using various combinations of waveplates and polarizers to produce the desired states, rather than using liquid crystal elements. This is an acceptable alternative to the use of liquid crystal retarders, and may be preferred if one wishes to construct apparatus for use in the infrared or ultraviolet spectral range, where the performance of liquid crystal retarders may not be high.

It is possible to assemble polarizers which express the required states, and to then cycle them into the optical path using mechanical switching means such as a filter wheel or slider. Alternatively, in embodiments that do not make use of $\chi_0$, one may simply rotate the axis of a single elliptical polarizer to produce the desired states, since $\chi_1$-$\chi_4$ all have the same degree of ellipticity and differ only in their azimuth angle.

Another alternative is to construct the invention using other types of electro-optic elements than liquid crystal retarders, such as Pockels cells, Faraday elements, and the like. Such modifications are explicitly intended to lie within the scope of the invention, and the construction of alternative elliptical polarizer apparatus will be understood by those skilled in the art of polarized optics and of instrument design. Indeed any element may be used to construct the elliptical polarizers provided that they achieve the desired polarization states, and that they suit the application at hand; the choice of one element over another can be made in terms of such factors as optical performance, aperture, cost, availability, and so on.

In all of the above embodiments, from N=2 through N=5, it is possible to utilize background measurements taken with the sample out to improve the measurement by correcting for instrumental polarization artifacts. To do so, one records the intensity that is obtained in each polarizer setting with no sample, and saves these background images. The background images need only be taken at intervals, and may be used to correct any number of sample images. Typically, they are taken when one expects that the apparatus may have drifted, such as due to a thermal change, or when using a different optical set-up such as a different objective lens.

The sequence for recording and utilizing background images is detailed in FIGS. 5 through 11, in flowchart format.

Thus while specific embodiments have been shown, it is understood that alternatives and equivalent constructions are possible, and that the invention can be used together with a variety of imaging systems, and in combination with image processing and data analysis techniques, as will be known by those skilled in these arts. Moreover, while there have shown and described and pointed out fundamental novel features of the invention as applied to preferred embodiments thereof, it will be understood that various omissions and substitutions and changes in the form and details of the methods described and devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. In addition, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. An apparatus for measuring retardance in a sample, comprising:
   a sample chamber for receiving the sample;
   an illuminator for providing an illumination light;
   optics for directing the illumination light toward the sample;
   a detector for measuring an intensity of light incident on the detector;
   optics for directing light that has interacted with the sample toward the detector;
   a first polarizer for selectively transmitting light that is substantially circularly polarized;
   a second polarizer for selectively transmitting light that has a selected elliptical polarization state;
   a controller for varying a selected elliptical polarization state of the second polarizer to correspond to a plural number of states $\chi_i$ with a chosen Poincare latitude and longitude within a distance $\epsilon$ of a chosen pole of a Poincare sphere; and
   a processor connected to the detector for determining the sample retardance from the measured incident light intensity obtained when the second polarizer is set to each of the states $\chi_i$;
   wherein none of the states $\chi_i$ corresponds to circular polarization.

2. The apparatus of claim 1, wherein the illumination light is transmitted by the sample.

3. The apparatus of claim 1, wherein the illumination light is reflected by the sample.

4. The apparatus of claim 1, wherein:
   the first polarizer is located between the illuminator and the sample chamber; and
   the second polarizer is located between the sample chamber and the detector.

5. The apparatus of claim 1, wherein:
   the second polarizer is located between the illuminator and the sample chamber; and
   the first polarizer is located between the sample chamber and the detector.

6. The apparatus of claim 1, wherein the number of states $\chi_i$ is 2.

7. The apparatus of claim 1, wherein the number of states $\chi_i$ is 3.

8. The apparatus of claim 1, wherein the number of states $\chi_i$ is 4.

9. The apparatus of claim 1, wherein the second polarizer comprises an electro-optic retarder element.

10. The apparatus of claim 1, wherein the second polarizer comprises at least one fixed retarder and mechanical switching means.

11. The apparatus of claim 1, wherein the illumination light is substantially monochromatic.

12. The apparatus of claim 1, wherein the illuminator comprises a broadband source and a filter.

13. The apparatus of claim 1, wherein $\epsilon$ is 35 degrees or less.

14. The apparatus of claim 1, wherein $\epsilon$ is 20 degrees or less.

15. A method for measuring retardance in a sample in a sample chamber, comprising the steps of:
   producing an illumination beam of light;
   directing the illumination beam toward the sample;
   collecting directed illumination light that has interacted with the sample to form a collected light beam;
   directing the collected light beam toward a photodetector;
   directing one of the illumination beam and the collected light beam through a circular polarizer;
   directing the other of the illumination beam and the collected light beam through a variable polarizer that expresses a plural number of elliptical polarization states $\chi_i$;

measuring an intensity of light incident on the photodetector during each of the plural states $\chi_i$; and calculating the retardance of the sample using the photodetector light intensity measurements;

wherein the number of states $\chi_i$ is four or less and none of the states $\chi_i$ is circular.

16. The method of claim 15, wherein each of the plural states $\chi_i$ lies within a distance $\epsilon$ from a chosen pole of the Poincare sphere.

17. The method of claim 16, wherein $\epsilon$ is 35 degrees or less.

18. The method of claim 16, wherein $\epsilon$ is 20 degrees or less.

19. The method of claim 15, further comprising the steps of:

measuring the intensity of light incident on the photodetector while the variable polarizer expresses a plurality of states $\chi_i$ and the sample is not present in the sample chamber; and using the measured intensities of light incident on the photodetector when the sample is not present to improve the calculation of sample retardance.

20. The method of claim 19, wherein said measuring the intensity of light with the sample not present in the sample chamber comprises measuring the light intensity with the sample replaced by a calibration target of substantially no retardance and a calibration target of known retardance.

* * * * *